(12) United States Patent
Flynn et al.

(10) Patent No.: US 7,678,426 B2
(45) Date of Patent: *Mar. 16, 2010

(54) PERFLUOROPOLYETHER AMIDE-LINKED PHOSPHONATES, PHOSPHATES, AND DERIVATIVES THEREOF

(75) Inventors: Richard M. Flynn, Mahtomedi, MN (US); Mark J. Pellerite, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 416 days.

This patent is subject to a terminal disclaimer.

(21) Appl. No.: 10/886,123

(22) Filed: Jul. 7, 2004

(65) Prior Publication Data

US 2005/0048288 A1 Mar. 3, 2005

Related U.S. Application Data

(60) Provisional application No. 60/496,837, filed on Aug. 21, 2003.

(51) Int. Cl.
*B05D 3/02* (2006.01)
*C07F 9/22* (2006.01)

(52) U.S. Cl. .......................... 427/384; 558/170; 562/15

(58) Field of Classification Search ................ 562/15; 558/170; 428/411.1, 422
See application file for complete search history.

(56) References Cited

U.S. PATENT DOCUMENTS

| | | | |
|---|---|---|---|
| 3,274,244 A | 9/1966 | Mackenzie | |
| 3,306,855 A | 2/1967 | Borecki | |
| 3,492,374 A | 1/1970 | Bleu et al. | |
| 3,646,085 A | 2/1972 | Bartlett | |
| 3,734,687 A * | 5/1973 | Gresham | 8/188 |
| 3,810,874 A | 5/1974 | Mitsch et al. | |
| 3,901,727 A * | 8/1975 | Loudas | 134/4 |
| 3,950,588 A | 4/1976 | McDougal | |
| 4,923,720 A | 5/1990 | Lee et al. | |
| 4,927,950 A * | 5/1990 | Hisamoto et al. | 556/419 |
| 5,027,742 A | 7/1991 | Lee et al. | |
| 5,032,279 A | 7/1991 | Lee | |
| 5,066,522 A | 11/1991 | Cole et al. | |
| 5,108,799 A | 4/1992 | Hoy et al. | |
| 5,132,446 A | 7/1992 | Tohzuka et al. | |
| 5,211,342 A | 5/1993 | Hoy et al. | |
| 5,227,008 A | 7/1993 | Klun et al. | |

(Continued)

FOREIGN PATENT DOCUMENTS

CA 761007 6/1967

(Continued)

OTHER PUBLICATIONS

J. Fluorine Chem., 95, 51 (1999).

(Continued)

*Primary Examiner*—Ramsey Zacharia
(74) *Attorney, Agent, or Firm*—Kathleen B. Gross; Daniel R. Pastirik; Jean A. Lown

(57) ABSTRACT

Perfluoropolyether amide-linked phosphonates and derivatives thereof are provided. Compositions containing perfluoropolyether amide-linked phosphonates or derivatives thereof, perfluoropolyether amide-linked phosphates or derivatives thereof, or combinations thereof are also provided. Additionally, articles, methods of making articles, and methods of reducing contaminant adhesion to a substrate are described.

23 Claims, 1 Drawing Sheet

U.S. PATENT DOCUMENTS

| | | |
|---|---|---|
| 5,256,318 A | 10/1993 | Masutani et al. |
| 5,274,159 A | 12/1993 | Pellerite et al. |
| 5,306,758 A | 4/1994 | Pellerite |
| 5,550,277 A | 8/1996 | Paciorek et al. |
| 5,851,674 A | 12/1998 | Pellerite et al. |
| 6,127,000 A | 10/2000 | Carbonell et al. |
| 6,177,357 B1 | 1/2001 | Lu |
| 6,184,187 B1 | 2/2001 | Howell et al. |
| 6,376,065 B1 | 4/2002 | Korba et al. |
| 6,403,211 B1 | 6/2002 | Yang et al. |
| 2003/0228469 A1 | 12/2003 | Boardman et al. |

FOREIGN PATENT DOCUMENTS

| | | |
|---|---|---|
| EP | 0 603 697 | 6/1994 |
| EP | 0 789 050 | 8/1997 |
| EP | 1 055 718 | 11/2000 |
| EP | 1 225 178 | 7/2002 |
| JP | 03-027079 | 1/2003 |
| WO | WO98/40439 | 9/1998 |
| WO | WO99/37720 | 7/1999 |

OTHER PUBLICATIONS

*Supercritical Fluids*, Encyclopedia of Chemical Technology, $4^{th}$ Edition, John Wiley and Sons, N.Y, vol. 23, pp. 453, 1997.
Z. Surf Interface Anal. 2002, 34, 148-154.
Surf Eng. 2002, 18, 228-232.
J. Phys. Chem. B2002, 106, 1728-1733.
Langmuir 1999, 15, 7605-7614.

* cited by examiner

PERFLUOROPOLYETHER AMIDE-LINKED PHOSPHONATES, PHOSPHATES, AND DERIVATIVES THEREOF

This application claims the benefit under 35 U.S.C. 199(e) of U.S. Provisional Application No. 60/496,837, filed 21 Aug. 2003.

BACKGROUND

Current product trends in electronics are requiring flexible circuits of finer and finer pitch. A repeating defect caused by small particles that adhere to a phototool during the imaging step of the flexible circuit making process may significantly reduce the product yield.

The fabrication of flexible circuits involves the creation of several layers of dielectric and conductive materials that are in intimate contact with layers adjacent to them. At least one of these layers may be patterned by selectively introducing material into or removing material from that layer. The pattern may be created by photolithographic processes. For example, a layer of photoresist material can be applied onto the surface of the layer to be patterned. A phototool having transparent and opaque areas in the form of the desired pattern can be used to selectively expose the photoresist to ultraviolet light. The light will either cause portions of the photoresist to undergo a crosslinking reaction in the exposed areas, as in the case of a negative photoresist, or to undergo a polymeric degradation reaction in the exposed areas, as is the case with a positive photoresist. An appropriate solvent may be used to remove the desired portion of the photoresist. The exposed underlying area may be etched away in the case of subtractive processing or added to in the case of additive processing. In either case the layer is patterned.

Photolithographic processes enable the creation of flexible circuits having excellent feature resolution as well as allowing high throughput during the manufacturing process. If different patterns are applied to different layers, the phototool must be correctly aligned on the photoresist layer. The phototool may be secured to the photoresist by clamping or by pulling a vacuum when the phototool is placed in contact with the photoresist during this photolithographic process.

However, defects in the pattern or the phototool are routinely experienced, especially when the phototool is used repeatedly to print several substrates consecutively without cleaning the phototool. Consequently, phototools must be inspected and cleaned regularly. This can affect the throughput of the lithographic process as well as introduce added cost if the defects cannot be eliminated and the phototools must be replaced.

Conventional phototools often have chrome and glass regions. Light can pass through the glass regions but not the chrome regions. Both glass and chrome are high surface energy materials, which can cause particles of the photoresist or dust to adhere to the phototool. When particles stick to the glass, light is absorbed and, as a result, does not reach the photoresist. This can result in inadequate exposure of a given area, which in turn creates defects. Furthermore, particles that adhere to the phototool can create a gap between the phototool and the photoresist surface, reducing resolution of the resulting image.

SUMMARY

Perfluoropolyether amide-linked phosphonates and derivatives thereof are provided. Compositions containing perfluoropolyether amide-linked phosphonates or derivatives thereof, perfluoropolyether amide-linked phosphates or derivatives thereof, or combinations thereof are also provided. Additionally, articles, methods of making articles, and methods of reducing contaminant adhesion to a substrate are disclosed. The compounds and compositions can be used, for example, to form a layer on the surface of a substrate such as a phototool during a photolithographic process. Such a layer can help minimize defects in products formed using a photolithographic process, can increase the throughput of a lithographic process, or a combination thereof.

In one aspect, compounds are provided according to Formula I:

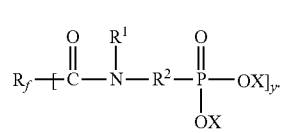

In Formula I, $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein R is unsubstituted or substituted with an alkyl, aryl, halo, or combinations thereof.

In another aspect, compositions are provided that include a hydrofluoroether and a compound according to Formula I, Formula II, or combinations thereof:

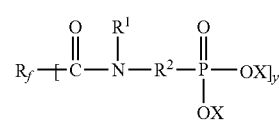

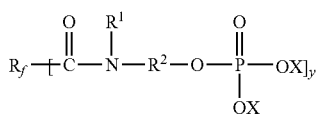

where $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof.

In a third aspect, compositions are provided that include a fluorinated silane and a compound according to Formula I, Formula II, or combinations thereof:

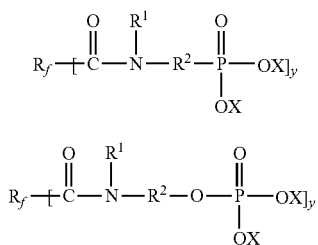

where $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof.

In a fourth aspect, an article is provided that includes a substrate and a compound according to Formula I attached to a surface of the substrate.

In a fifth aspect, a method is provided for making an article. The method includes applying a coating composition to a surface of a substrate. In one embodiment, the coating composition includes a compound of Formula I. In a second embodiment, the coating composition includes a first component selected from a hydrofluoroether, fluorinated silane, or combinations thereof and a second component selected from a compound of Formula I, Formula II, or combinations thereof.

In a sixth aspect, a method is provided for reducing contaminant adhesion to a substrate. The method includes applying a coating composition to a surface of the substrate. In one embodiment, the coating composition includes a compound of Formula I. In a second embodiment, the coating composition includes a first component selected from a hydrofluoroether, fluorinated silane, or combinations thereof and a second component selected from a compound of Formula I, Formula II, or combinations thereof.

The above summary is not intended to describe each disclosed embodiment or every implementation of the present invention. The detailed description section that follows more particularly exemplifies these embodiments.

BRIEF DESCRIPTION OF THE DRAWING

The above aspects may be more completely understood in consideration of the following detailed description of various embodiments in connection with the accompanying drawing, in which.

Figure 1:
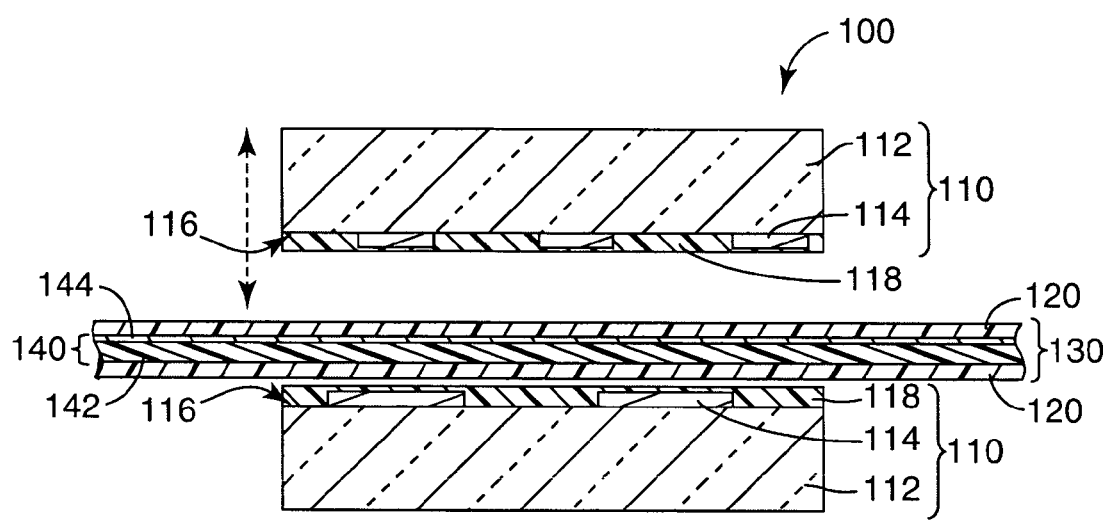
FIG. 1 is a cross sectional view of a simple photolithography apparatus.

It should be understood that the intention is not to limit use of the compounds and compositions to the particular applications shown. To the contrary, the intention is to only exemplify some uses for the compounds and compositions.

DETAILED DESCRIPTION

Perfluoropolyether amide-linked phosphonates and derivatives thereof are provided. Compositions containing perfluoropolyether amide-linked phosphonates or derivatives thereof, perfluoropolyether amide-linked phosphates or derivatives thereof, or combinations thereof are also provided. Additionally, articles, methods of making articles, and methods of reducing contaminant adhesion to a substrate are disclosed. The compounds and compositions can be used, for example, for coating a substrate such as a phototool in a photolithographic process.

Definitions

As used herein, the terms "a", "an", and "the" are used interchangeably with "at least one" to mean one or more of the elements being described.

As used herein, the term "acyl" refers to a group of formula R(CO)— where (CO) indicates that the carbon is attached to the oxygen with a double bond and R is an alkyl group.

As used herein, the term "acyloxy" refers to a group of formula R(CO)O— where R is an alkyl group.

As used herein, the term "alkali metal" refers to a sodium ion, potassium ion, or lithium ion.

As used herein, the term "alkane" refers to saturated hydrocarbons that are linear, branched, cyclic, or combinations thereof. The alkane typically has 1 to 30 carbon atoms. In some embodiments, the alkane has 1 to 20, 1 to 10, 1 to 8, 1 to 6, 1 to 4, or 1 to 3 carbon atoms.

As used herein, the term "alkoxy" refers to a group of formula —OR where R is an alkyl group.

As used herein, the term "alkyl" refers to a monovalent moiety formed by abstraction of a hydrogen atom from an alkane. The alkyl can have a linear structure, branched structure, cyclic structure, or combinations thereof. A cycloalkyl is a cyclic alkyl and is a subset of an alkyl group.

As used herein, the term "alkylene" refers to a divalent moiety formed by abstraction of two hydrogen atoms from an alkane. The alkylene can have a linear structure, branched structure, cyclic structure, or combinations thereof.

As used herein, the term "aryl" refers to a monovalent moiety of a carbocyclic aromatic compound having one to five connected rings, multiple fused rings, or combinations thereof. In some embodiments, the aryl group has four rings, three rings, two rings, or one ring. For example, the aryl group can be phenyl.

As used herein, the term "arylene" refers to a divalent moiety of a carbocyclic aromatic compound having one to five connected rings, multiple fused rings, or combinations thereof. In some embodiments, the arylene group has four rings, three rings, two rings, or one ring. For example, the arylene group can be phenylene.

As used herein, the term "carbonyl" refers to a divalent group of formula —(CO)— where the carbon is attached to the oxygen with a double bond.

As used herein, the term "carbonyloxy" refers to a divalent group of formula —(CO)O—.

As used herein, the term "carbonylimino" refers to a divalent group of formula —(CO)$NR^d$— where $R^d$ is hydrogen or alkyl.

As used herein, the term "fluoroalkyl" refers to an alkyl group in which at least one of the hydrogen atoms is replaced with a fluorine atom.

As used herein, the term "fluoroether" refers to a compound or group having two saturated or unsaturated hydrocarbon groups linked with an oxygen atom (i.e., there is one catenated oxygen atom). At least one of the hydrocarbon groups has at least one hydrogen atom replaced with a fluorine atom. The hydrocarbon groups can have a linear structure, branched structure, cyclic structure, or combinations thereof.

As used herein, the term "fluoropolyether" refers to a compound or group having three or more saturated or unsaturated hydrocarbon groups linked with oxygen atoms (i.e., there are at least two catenated oxygen atoms). At least one, and typically two or more, of the hydrocarbon groups has at least one hydrogen atom replaced with a fluorine atom. The hydrocarbon groups can have a linear structure, branched structure, cyclic structure, or combinations thereof.

As used herein, the term "halo" refers to chlorine, bromine, iodine, or fluorine.

As used herein, the term "heteroalkane" refers to an alkane having one or more carbon atoms replaced with a sulfur, oxygen, or $NR^d$ where $R^d$ is hydrogen or alkyl. The heteroalkane can be linear, branched, cyclic, or combinations thereof and typically includes up to about 30 carbon atoms. In some embodiments, the heteroalkane includes no more than 20 carbon atoms, no more than 10 carbon atoms, no more than 8 carbon atoms, no more than 6 carbon atoms, or no more than 4 carbon atoms. Ethers and polyethers are subsets of a heteroalkane.

As used herein, the term "heteroalkyl" refers to a monovalent moiety formed by abstraction of a hydrogen atom from a heteroalkane.

As used herein, the term "heteroalkylene" refers to a divalent moiety formed by abstraction of two hydrogen atoms from a heteroalkane.

As used herein, the term "perfluoroalkane" refers to an alkane in which all of the hydrogen atoms are replaced with fluorine atoms.

As used herein, the term "perfluoroalkanediyl" refers to a divalent moiety formed by abstraction of two fluorine atoms from a perfluoroalkane where the radical centers are located on different carbon atoms.

As used herein, the term "perfluoroalkanetriyl" refers to a trivalent moiety formed by abstraction of three fluorine atoms from a perfluoroalkane.

As used herein, the term "perfluoroalkyl" refers to an alkyl group in which all of the hydrogen atoms are replaced with fluorine atoms.

As used herein, the term "perfluoroalkylidene" refers to a divalent moiety formed by abstraction of two fluorine atoms from a perfluoroalkane where the radical centers are on the same carbon atom.

As used herein, the term "perfluoroalkoxy" refers to an alkoxy group in which all of the hydrogen atoms are replaced with fluorine atoms.

As used herein, the term "perfluoroether" refers to a fluoroether in which all of the hydrogens on all of the hydrocarbon groups are replaced with fluorine atoms.

As used herein, the term "perfluoropolyether" refers to a fluoropolyether in which all of the hydrogens on all of the hydrocarbon groups are replaced with fluorine atoms.

As used herein, the term "phosphonic acid" refers to a group, or compound that includes a group, of formula —(P=O)(OH)$_2$ attached directly to a carbon atom As used herein, the term "phosphonate" refers to a group, or compound that includes a group, of formula —(P=O)(OX)$_2$ attached directly to a carbon atom where X is selected from an alkali, or a five to seven membered heterocyclic group having a positively charged nitrogen atom. Phosphonates can be esters or salts of the corresponding phosphonic acid.

As used herein, the term "phosphate" refers to a salt or ester of formula —O(P=O)(OX)$_2$ attached directly to a carbon atom where X is selected from hydrogen, alkali metal, alkyl, cycloalkyl, ammonium, ammonium substituted with an alkyl or cycloalkyl, or a five to seven membered heterocyclic group having a positively charged nitrogen atom.

As used herein, the term "phototool" refers to any type of mask that is used in conjunction with radiation exposure to pattern a layer of radiation-sensitive material by blocking portions of the layer from radiation.

As used herein, the term "substrate" refers to a solid support. The substrates can be porous or non-porous, rigid or flexible, transparent or opaque, clear or colored, and reflective or non-reflective. Suitable substrate materials include polymeric materials, glasses, ceramics, metals, or combinations thereof.

As used herein, the term "sulfonamido" refers to a group of formula —SO$_2$NR$^a$— where R$^a$ is an alkyl or aryl.

Compounds

Compounds are provided according to Formula I:

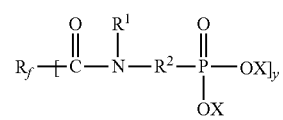

where $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof.

The group $R^1$ in Formula I can be hydrogen or an alkyl. In some embodiments, $R^1$ is a $C_1$ to $C_4$ alkyl.

Each X group in Formula I independently can be hydrogen, alkyl, cycloalkyl, alkali metal, ammonium, ammonium substituted with an alkyl or cycloalkyl, or a five to seven membered heterocyclic group having a positively charged nitrogen atom. When each X is hydrogen, the compound according to Formula I is a phosphonic acid. The compound according to Formula I is an ester when at least one X is an alkyl group. Exemplary alkyl groups include those having 1 to 4 carbon atoms. The alkyl group can be linear, branched, or cyclic.

The compound according to Formula I is a salt when at least one X is an alkali metal, ammonium, ammonium substituted with an alkyl or cycloalkyl, or a five to seven membered heterocyclic group having a positively charged nitrogen atom. Exemplary alkali metals include sodium, potassium, and lithium. Exemplary substituted ammonium ions include, but are not limited to, tetraalkylammonium ions. The alkyl substituents on the ammonium ion can be linear, branched, or cyclic. Exemplary five or six membered heterocyclic groups having a positively charged nitrogen atom include, but are not limited to, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, oxathiazolium ion, pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion.

The $R^2$ group includes a divalent group selected from an alkylene, arylene, heteroalkylene, or combinations thereof and an optional divalent group selected from carbonyl, carbonyloxy, carbonylimino, sulfonamido, or combinations thereof. $R^2$ can be unsubstituted or substituted with an alkyl, aryl, halo, or combinations thereof. The $R^2$ group typically has no more than 30 carbon atoms. In some compounds, the $R^2$ group has no more than 20 carbon atoms, no more than 10 carbon atoms, no more than 6 carbon atoms, or no more than 4 carbon atoms. For example, $R^2$ can be an alkylene, an alkylene substituted with an aryl group, or an alkylene in combination with an arylene. In some exemplary compounds, the $R^2$ group is a phenylene group connected to an alkylene group where the alkylene group has 1 to 6 carbon atoms. In other exemplary compounds, the $R^2$ group is an alkylene group having 1 to 6 carbon atoms that is unsubstituted or substituted with a phenyl or alkyl group.

The perfluoropolyether group $R_f$ can be linear, branched, cyclic, or combinations thereof and can be saturated or unsaturated. The perfluoropolyether has at least two catenated oxygen heteroatoms. Exemplary perfluoropolyethers include, but are not limited to, those that have perfluorinated repeating units selected from the group of —$(C_pF_{2p})$—, —$(C_pF_{2p}O)$—, —$(CF(Z))$—, —$(CF(Z)O)$—, —$(CF(Z)C_pF_{2p}O)$—, —$(C_pF_{2p}CF(Z)O)$—, —$(CF_2CF(Z)O)$—, or combinations thereof. In these repeating units, p is typically an integer of 1 to 10. In some embodiments, p is an integer of 1 to 8, 1 to 6, 1 to 4, or 1 to 3. The Z group can be a perfluoroalkyl group, perfluoroether group, perfluoropolyether, or a perfluoroalkoxy group that has a linear structure, branched structure, cyclic structure, or combinations thereof. The Z group typically has no more than 12 carbon atoms, no more than 10 carbon atoms, no more than 8 carbon atoms, no more than 6 carbon toms, no more than 4 carbon atoms, no more than 3 carbon atoms, no more than 2 carbon atoms, or no more than 1 carbon atom. In some embodiments, the Z group can have no more than 4, no more than 3, no more than 2, no more than 1, or no oxygen atoms. In these perfluoropolyether structures, different repeating units can be combined in a block or random arrangement to form the $R_f$ group.

$R_f$ can be monovalent (i.e., y is 1 in Formula I) or divalent (i.e., y is 2 in Formula I). Where the perfluoropolyether group $R_f$ is monovalent, the terminal group of the perfluoropolyether group $R_f$ can be $(C_pF_{2p+1})$—, $(C_pF_{2p+1}O)$—, for example, where p is an integer of 1 to 10, 1 to 8, 1 to 6, 1 to 4, or 1 to 3. Some exemplary monovalent perfluoropolyether groups $R_f$ include, but are not limited to, $C_3F_7O(CF(CF_3)CF_2O)_nCF(CF_3)$—, $C_3F_7O(CF_2CF_2CF_2O)_nCF_2CF_2$—, and $CF_3O(C_2F_4O)_nCF_2$—wherein n has an average value of 0 to 50, 1 to 50, 3 to 30, 3 to 15, or 3 to 10.

Other exemplary monovalent perfluoropolyether groups $R_f$ include, but are not limited to $CF_3O(CF_2O)_q(C_2F_4O)_nCF_2$— and $F(CF_2)_3O(C_4F_8O)_n(CF_2)_3$—, where q can have an average value of 0 to 50, 1 to 50, 3 to 30, 3 to 15, or 3 to 10; and n can have an average value of 0 to 50, 3 to 30, 3 to 15, or 3 to 10.

Some exemplary divalent perfluoropolyether groups $R_f$ include, but are not limited to —$CF_2O(CF_2O)_q(C_2F_4O)_nCF_2$—, —$CF_2O(C_2F_4O)_nCF_2$—, —$(CF_2)_3O(C_4F_8O)_n(CF_2)_3$—, and —$CF(CF_3)(OCF_2CF(CF_3))_sOC_rF_{2t}O(CF(CF_3)CF_2O)_nCF(CF_3)$— where q can have an average value of 0 to 50, 1 to 50, 3 to 30, 3 to 15, or 3 to 10; n can have an average value of 0 to 50, 3 to 30, 3 to 15, or 3 to 10; s can have an average value of 0 to 50, 1 to 50, 3 to 30, 3 to 15, or 3 to 10; the sum of n and s (i.e., n+s) can have an average value of 0 to 50 or 4 to 40; the sum of q and n (i.e., q+n) can be greater than 0; and t can be an integer of 2 to 6.

As synthesized, the perfluoropolyether amide-linked phosphonates and derivatives thereof according to Formula I typically are mixtures having different perfluoropolyether groups $R_f$ (i.e., the compound is not synthesized as a single compound but a mixture of compounds with different $R_f$ groups). For example, the values of q, n, and s can vary as long as the mixture has a number average molecular weight of at least 400 g/mole. Suitable mixtures of perfluoropolyether amide-linked phosphonates and derivatives thereof typically have a number average molecular weight of at least about 400, at least 800, or at least about 1000 g/mole. Mixtures of different perfluoropolyether amide-linked phosphonates and derivatives thereof often have a molecular weight (number average) of 400 to 10000 g/mole, 800 to 4000 g/mole, or 1000 to 3000 g/mole.

Specific examples of compounds according to Formula I include:

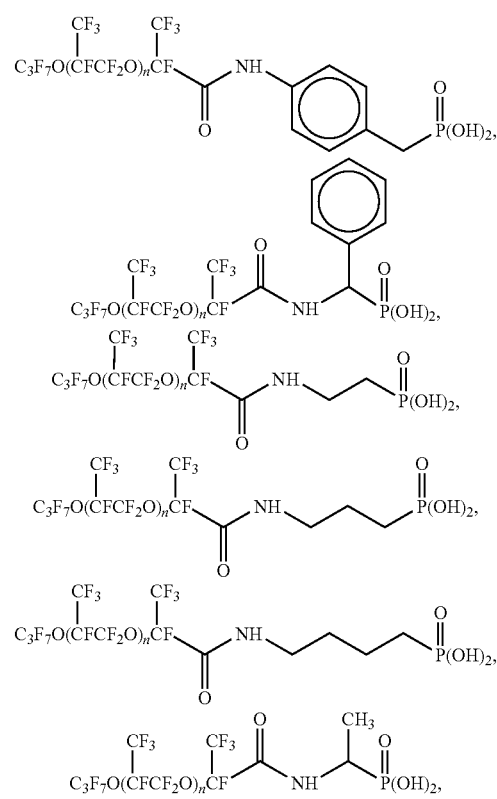

and derivatives thereof where n has an average value of 0 to 50, 1 to 50, 3 to 30, 3 to 15, or 3 to 10. Suitable derivatives include salts and esters of the phosphonic acids.

Compositions

Compositions are provided that include a hydrofluoroether and a compound according to Formula I, Formula II, or combinations thereof:

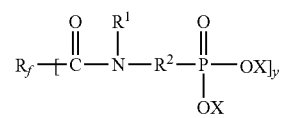

I

-continued

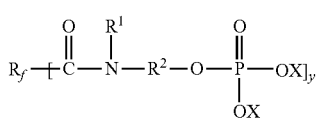

II where $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof. Compounds according to Formula II are perfluoropolyether amide-linked phosphates and derivatives thereof.

Suitable hydrofluoroethers, for example, can be of Formula III:

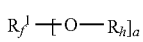

III where a is an integer of 1 to 3; the group $R_f^1$ is a monovalent, divalent, or trivalent moiety of a perfluoroalkane, perfluoroether, or perfluoropolyether; and $R_h$ is an alkyl or heteroalkyl. The $R_f^1$ group can have a linear structure, branched structure, cyclic structure, or combinations thereof. Likewise, the $R_h$ group can have a linear structure, branched structure, cyclic structure, or combinations thereof. The sum of the number of carbon atoms in the group $R_f^1$ and the number of carbon atoms in the group $R_h$ will typically be greater than or equal to four.

The $R_f^1$ group is monovalent when a is equal to 1, divalent when a is equal to 2, and trivalent when a is equal to 3. The $R_f^1$ group typically contains no more than 30 carbon atoms, no more than 20 carbon atoms, no more than 15 carbon atoms, no more than 12 carbon atoms, or no more than 8 carbon atoms. The $R_f^1$ group can include at least 1, at least 2, at least 3, or at least 4 carbon atoms. In some applications, $R_f^1$ includes 4 to 9 carbon atoms, 4 to 8, 4 to 7, 5 to 7, or 5 to 6 carbon atoms. For a divalent $R_f^1$ group, the radical centers can be on the same or different carbon atoms. For a trivalent $R_f^1$ group, the radical centers can each be on a different carbon atom or two of the radical centers can be on the same carbon atom.

In some compounds according to Formula III where a is equal to 1, the group $R_f^1$ can, for example, be (1) a linear or branched perfluoroalkyl group having from two to about fifteen carbon atoms, (2) a perfluorocycloalkyl-containing perfluoroalkyl group having from five to about fifteen carbon atoms, or (3) a perfluorocycloalkyl group having from three to about twelve carbon atoms. A cyclic structure can be optionally substituted with a perfluoroalkyl group having 1 to 4 carbon atoms.

In some compounds according to Formula II where a is equal to 2, the group $R_f^1$ can be (1) a linear or branched perfluoroalkanediyl group, (2) a perfluoroalkylidene group having from two to about fifteen carbon atoms, (3) a perfluorocycloalkyl- or perfluorocycloalkylene-containing perfluoroalkanediyl or perfluoroalkylidene group having five to about fifteen carbon atoms, or (4) a perfluorocycloalkanediyl group or perfluorocycloalkylidene group having three to about twelve carbon atoms. A cyclic structure can be optionally substituted with a perfluoroalkyl group having 1 to 4 carbon atoms.

In some compounds according to Formula III when a is equal to 3, the group $R_f^1$ can be (1) a linear or branched perfluoroalkanetriyl group having from two to about fifteen carbon atoms, (2) a perfluorocycloalkyl- or perfluorocycloalkylene-containing group from about six to fifteen carbon atoms, or (3) a perfluorocycloalkanetriyl group having from three to about twelve carbon atoms. A cyclic structure can be optionally substituted with a perfluoroalkyl group having 1 to 4 carbon atoms.

In compounds according to Formula III, each $R_h$ group can independently be an alkyl or a heteroalkyl. Each of the groups usable as $R_h$ can have a linear structure, branched structure, cyclic structure, or combinations thereof. In some embodiments where $R_h$ is a heteroalkyl group, the heteroalkyl moiety can be an ether group or a polyether group. The alkyl or heteroalkyl group used as the group $R_h$ often will have no more than twenty carbon atoms, no more than ten carbon atoms, or no more than eight carbon atoms. In some compounds according to Formula III, the $R_h$ group can have one to eight carbon atoms. For example, the group $R_h$ in the compounds according to Formula III can be a cycloalkyl-containing alkyl group having from four to about eight carbon atoms or a cycloalkyl group having from three to about eight carbon atoms.

Some specific exemplary hydrofluoroethers that fall within the scope of the compound according to Formula III include, but are not limited to, methyl perfluoro-n-butyl ether, methyl perfluoroisobutyl ether, ethyl perfluoro-n-butyl ether, ethyl perfluoroisobutyl ether, or combinations thereof.

Compositions are also provided that include a fluorinated silane and a compound according to Formula I, Formula II, or combinations thereof:

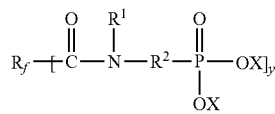

I

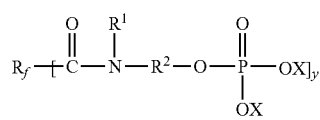

II where $R_f$ is a monovalent or divalent perfluoropolyether group; y is equal to 1 or 2; each X is independently hydrogen, alkyl, cycloalkyl, alkali metal, ammonium, ammonium substituted with an alkyl or cycloalkyl, or a five to seven membered heterocyclic group having a positively charged nitrogen atom; $R^1$ is hydrogen or alkyl; and $R^2$ includes a divalent group selected from an alkylene, arylene, heteroalkylene, or combinations thereof and an optional divalent group selected from carbonyl, carbonyloxy, carbonylimino, sulfonamido, or combinations thereof, wherein R is unsubstituted or substituted with an alkyl, aryl, halo, or combinations thereof. The groups $R_f$, $R^1$, $R^2$, and X are further described above.

Suitable fluorinated silanes include compounds according to Formula IV:

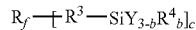

where $R_f$ is a monovalent or divalent perfluoropolyether group; c is an integer of 1 to 2; b is an integer of 0 or 1; $R^3$ is selected from an alkylene, arylene, heteroalkylene, carbonyl, carbonyloxy, carbonylimino, sulfonamido, or combinations thereof that is unsubstituted or substituted with an alkyl, aryl, halo, or combinations thereof; $R^4$ is an alkyl group; and Y is selected from an alkoxy or acyloxy.

$R_f$ is the same as defined above for Formula I.

The $R^3$ group in Formula IV is selected from an alkylene, arylene, heteroalkylene, carbonyl, carbonyloxy, carbonylimino, sulfonamido, or combinations thereof that is unsubstituted or substituted with an alkyl, aryl, or halo group. In some embodiments, $R^3$ is an alkylene, an alkylene substituted with an aryl group, or an alkylene in combination with an arylene. The $R^3$ group typically has no more than 30 carbon atoms. For example, the $R^3$ group can have 2 to 20 carbon atoms, 2 to 16 carbon atoms, or 3 to 10 carbon atoms. In some exemplary fluorinated silanes, the $R^3$ group is —C(O)NH$(CH_2)_3$— or —$CH_2O(CH_2)_3$—.

The $R^4$ group in Formula IV is an alkyl group. For example, $R^4$ is an alkyl having no more than 10 carbon atoms, no more than 6 carbon atoms, or no more than 4 carbon atoms. In some examples, the $R^4$ group is a $C_1$ to $C_4$ alkyl.

The Y group in Formula IV is selected from an alkoxy or acyloxy. Suitable alkoxy groups typically have no more than 10, no more than 6, or no more than 4 carbon atoms. In some examples Y is a $C_1$ to $C_4$ alkoxy. In a specific example, b is equal to 0 and Y is an alkoxy group having 1 to 4 carbon atoms. Suitable acyloxy groups include those have the formula —OC(O)$R^5$ where $R^5$ is an alkyl group. In some compounds, $R^5$ is a $C_1$ to $C_4$ alkyl group.

Suitable fluorinated silanes according to Formula IV typically have a number average molecular weight of at least about 400, or at least about 1000. The compounds of Formula IV can be synthesized using standard techniques. For example, commercially available or readily synthesized perfluoropolyether esters can be combined with a functionalized alkoxysilane, such as a 3-aminopropylalkoxysilane, as described in U.S. Pat. No. 3,810,874 (see column 7, line 41 to column 8, line 49).

Examples of fluorinated silanes include, but are not limited to, the following structures: $QCF_2O(CF_2O)_q(C_2F_4O)_nCF_2Q$, $C_3F_7O(CF(CF_3)CF_2O)_nCF(CF_3)Q$, $QCF(CF_3)(OCF_2CF(CF_3))_sOC_pF_{2t}O(CF(CF_3)CF_2O)_nCF(CF_3)Q$, $QCF_2O(C_2F_4O)_nCF_2Q$, $CF_3O(C_2F_4O)_nCF_2Q$, and $Q(CF_2)_3O(C_4F_8O)_n(CF_2)_3Q$, where q has an average value of 0 to 50, 1 to 50, 3 to 30, 3 to 15, or 3 to 10; n has an average value of 0 to 50, 3 to 30, 3 to 15, or 3 to 10; s has an average value of 0 to 50, 1 to 50, 3 to 30, 3 to 15, or 3 to 10; the sum (n+s) has an average value of 0 to 50 or 4 to 40; the sum (q+n) is greater than 0; and t is an integer of 2 to 6. Q is —$R^3$—Si$Y_{3-b}R^4_b$ as defined above in Formula IV or a non-silane-containing terminal group when c is equal to one. The non-silane-containing terminal group can be $((C_pF_{2p+1})$—, $(X'C_pF_{2p}O)$—, or $(C_pF_{2p+1}O)$— wherein X' is H, Cl, or Br), with the proviso that at least one Q group per molecule is a silane.

In other fluorinated silanes, the $R^3$ group includes nitrogen. In some embodiments, at least one Q group per molecule is —C(O)NH$(CH_2)_3$Si$(OR)_3$ (wherein R is methyl, ethyl, or mixtures thereof), and the other Q group, if not a silane, is $OCF_3$, or $OC_3F_7$.

Articles and Methods

Another aspect of the invention provides an article that includes a substrate and a compound according to Formula I attached to a surface of the substrate. Compounds of Formula I are the same as described above.

Yet another aspect of the invention provides a method of making an article that includes applying a coating composition to a surface of a substrate. In one embodiment, the coating composition includes a compound of Formula I. In a second embodiment, the coating composition includes a first component selected from a hydrofluoroether, fluorinated silane, or combinations thereof and a second component selected from a compound of Formula I, Formula II, or combinations thereof. Compounds of Formula I and Formula II are the same as described above.

In some applications, the compounds of Formula I, Formula II, or combinations thereof can form a self-assembled monolayer on a substrate. For example, compounds of Formula I, Formula II, or combinations thereof can form a self-assembled monolayer on a metal-containing substrate. The metal-containing layer can include metals, metal oxides, or a combination thereof. Exemplary metal-containing substrates can include gold, platinum, chromium, aluminum, copper, silver, titanium, indium, germanium, tin, nickel, indium tin, or combinations thereof. These compounds can also form a self-assembled monolayer on glass and quartz, but typically adhere more readily to metal-containing substrates such as metal oxides. Self-assembled monolayers are generally thin, on the order of 10 nm or less, and typically do not significantly alter the optical or surface structural properties of the substrate. In many embodiments, the self-assembled layer has a thickness of about 1 nm to about 10 nm. In at least some embodiments, the layer is about 6 nm thick.

A coating including a compound of Formula I, Formula II, or combinations thereof can be applied to the surface of substrate to provide a low energy surface. Another aspect of the invention provides a method of reducing contaminant adhesion to a substrate that includes applying a coating composition to a surface of the substrate. In one embodiment, the coating composition includes a compound of Formula I. In a second embodiment, the coating composition includes a first component selected from a hydrofluoroether, fluorinated silane, or combinations thereof and a second component selected from a compound of Formula I, Formula II, or combinations thereof. Compounds of Formula I and Formula II are the same as described above.

In one embodiment of making an article, the substrate is a phototool. A coating of Formula I, Formula II, or combinations thereof on the surface of a phototool can inhibit dirt and other particles from adhering to the phototool surface. The coating can reduce the incidence of imaging defects during photolithographic processes, such as those used to make flexible circuits. The ability to prevent adhesion of particles to the phototool allows for better yields on fine pitch flexible circuits.

The fabrication of flexible circuits involves the creation of several layers of dielectric and conductive materials that are in intimate contact. At least one of these layers may be patterned by selectively introducing material or removing material. Patterned layers can be used to form circuit traces or features in the dielectric film such as windows, vias, etc. The pattern may be created by photolithographic processes. An image of the desired pattern is created by shining UV light through a phototool having the desired pattern onto a suitable receptor material, e.g., photoresist, which is in contact with the layer to be patterned.

A phototool includes a UV-transparent base material such as glass, quartz, or the like with a patterned UV-opaque material such as chrome, chrome oxide, or the like on a surface of the UV-transparent base material.

In one method of applying a coating to a phototool, a layer of a coating composition including a compound of Formula I, Formula II, or combinations thereof diluted in a suitable solvent (e.g., a hydrofluoroether) is applied to the phototool surface by a conventional coating process, such as spray coating, spin coating, dip coating, or the like. A fluorinated silane may also be included in the applied coating. The coating may then be air dried to remove the solvent, followed by baking in the oven, typically at a temperature of about 100° C. to about 150° C. for about 30 minutes, to remove any residual solvent, induce crosslinking of the perfluoropolyether silane, and enhance the bonding of the coating to the phototool surface.

These coated phototools may be used in photolithographic processes, such as those used to pattern metal and dielectric layers of a flexible circuit. In a photolithographic process, the patterned side of the phototool is brought into contact with a UV-receptor material. When UV light is transmitted toward the patterned phototool, the light passes through the transparent regions, but is reflected by the opaque regions, thereby exposing selected portions of the UV-receptor material to the light. After exposure, the phototool is lifted from the surface of the UV-receptor material, preferably without any sticking of the UV-receptor material or other foreign material to the phototool.

The UV-receptor material is typically a photoresist. For example, a layer of photoresist material is applied onto the surface of a flexible circuit layer to be patterned. The UV light that passes through the phototool is absorbed by the photoresist. The light will either cause the exposed portions of the photoresist to undergo a crosslinking reaction, as in the case of a negative photoresist, or will cause a polymeric degradation reaction to break down the polymer structure in the exposed areas, as is the case with a positive photoresist. The desired portion of the photoresist may then be removed by an appropriate solvent. The flexible circuits may then be processed by conventional methods, such as those described in U.S. Pat. No. 5,227,008; 6,177,357; or 6,403,211. For example, the exposed underlying area may be etched away in the case of subtractive processing or dielectric patterning, or material may be added in the case of additive processing.

FIG. 1 is a cross sectional view of a simple photolithography apparatus 100. The photolithography apparatus 100 includes at least one phototool 110, layered circuit substrate 130 which contains at least one layer of photoresist 120 and base layer 140. Base layer 140 is made of polymer (typically polyimide) layer 142, and metal (typically copper) layer 144. Phototool 110 includes a transparent material 112, typically of glass or quartz, with coated regions of opaque material 114, typically chromium having an oxide surface, interspersed on a surface of transparent material 112 in a manner well known to those skilled in the art. A layer of low surface energy material such as a compound of Formula I, II, or combinations thereof 118 can be applied to surface 116 of the transparent material 112 (including opaque material 114).

The compounds according to Formula I and Formula II typically have molecular weights in the range of 400 to 5000, more preferably 1000 to 3000.

Exemplary compounds according to Formula I that can be applied as a layer to a phototool include, but are not limited to, compounds such as

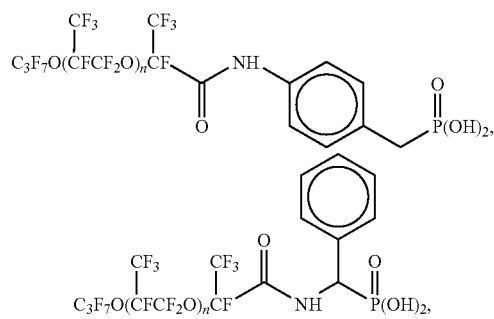

or derivatives thereof, where n has an average value of 3 to 30, 3 to 15, or 3 to 10.

Other exemplary compounds according to Formula I include, but are not limited to, compounds such as

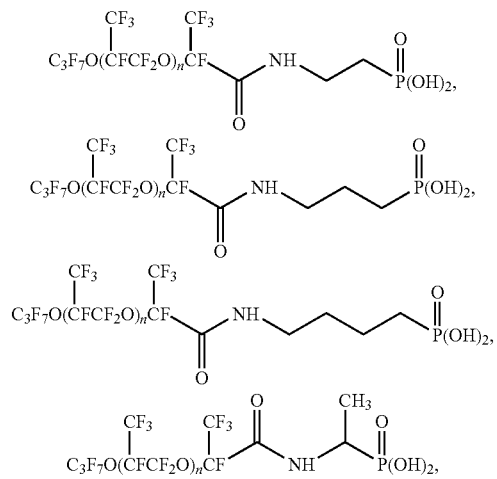

or derivatives thereof, where n has an average value of 3 to 30, 3 to 15, or 3 to 10.

Exemplary compounds according to Formula II that can be applied as a layer to a phototool include, but are not limited to, compounds such as

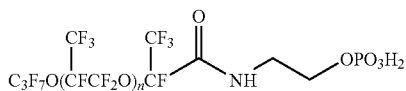

or derivatives thereof, where n has an average value of 3 to 30, 3 to 15, or 3 to 10.

In at least one embodiment, a compound according to Formula I, II, or combinations thereof forms a self-assembled monolayer on the transparent or opaque surfaces of the phototool. Self-assembled monolayers are particularly likely to form on metal-containing materials such as gold, platinum, chromium, aluminum, copper, indium, tin, silver, titanium, germanium, and nickel. The metal-containing materials can be metals, metal oxides, or a combination thereof. The self-assembled monolayers can also form on glass and quartz, but adhere more readily to metal oxides. Self-assembled monolayers often do not significantly alter the optical or surface structural properties of the original substrate. In most embodiments the compounds according to Formula I, II, or combinations thereof form a layer that is about 1 nm to about 10 nm thick. In at least one embodiment, the layer is about 6 nm thick.

Although the compounds according to Formula I, II, or combinations thereof can adhere to UV-transparent materials, such as glass, in addition to UV-opaque materials, such as chrome oxide, fluorinated silanes typically adhere to glass better. Accordingly, the compounds according to Formula I, II, or combinations thereof may be used alone or with a fluorinated silane.

Suitable fluorinated silanes include compounds according to Formula IV:

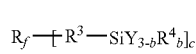

where $R_f$ is a monovalent or divalent perfluoropolyether group; c is an integer of 1 to 2; b is an integer of 0 or 1; $R^3$ is selected from an alkylene, arylene, heteroalkylene, carbonyl, carbonyloxy, carbonylimino, sulfonamido, or combinations thereof that is unsubstituted or substituted with an alkyl, aryl, halo, or combinations thereof, $R^4$ is an alkyl group; and Y is selected from alkoxy or acyloxy.

Compositions that include the compounds of Formula I, II, or combinations may be applied in any one of several conventional ways, such as spin coating, spraying, dipping, or vapor deposition. The compounds of Formula I, II, or combinations thereof are often soluble (or dispersible) in hydrofluoroethers such as 3M Novec™ Engineered Fluid HFE-7100 ($C_4F_9OCH_3$) which is a mixture of two inseparable isomers with essentially identical properties; or other organic solvents such as isopropanol. This solubility allows uniform films of excess material to be applied by spray or spin coating from a solution. The substrate can then be heated to accelerate monolayer formation, and the excess can be rinsed or wiped away leaving a monolayer film.

The solvent(s) used to apply the coating composition typically include those that are substantially inert (i.e., substantially nonreactive with the compounds of Formula I, II, or combinations thereof and fluorinated silanes), aprotic, and capable of dispersing or dissolving these materials. In some embodiments, the solvents substantially completely dissolve the compounds according to Formula I, II, or combinations thereof and fluorinated silanes. Examples of appropriate solvents include, but are not limited to, fluorinated hydrocarbons, particularly fluorine-substituted alkanes, ethers, particularly alkyl perfluoroalkyl ethers, and hydrochlorofluoro alkanes and ethers. Mixtures of such solvents can be used.

In some applications, the solvent is a hydrofluoroether. Suitable hydrofluoroethers can be represented by the following general Formula III:

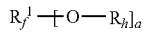

where a is an integer of 1 to 3, $R_f^1$ is a monovalent, divalent, or trivalent radical of a perfluoroalkane, perfluoroether, or perfluoropolyether that is linear, branched, cyclic, or combinations thereof; and $R^h$ an alkyl or heteroalkyl group that is linear, branched, cyclic, or combinations thereof. For example, the hydrofluoroether can be methyl perfluorobutyl ether or ethyl perfluorobutyl ether.

EXAMPLES

Example 1

The procedure disclosed in *J. Fluorine Chem.*, 95, 51 (1999), was followed for the preparation of the phosphate compound of the following formula:

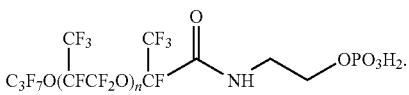

The alcohol $C_3F_7O[CF(CF_3)CF_2O]CF(CF_3)$ $CONHC_2H_4OH$ was prepared by treatment of $C_3F_7O[CF(CF_3)CF_2O]_nCF(CF_3)COOCH_3$ (prepared by reaction of the corresponding acyl fluoride with excess methanol) with excess 2-aminoethanol. Pyrophosphoric acid (25.5 g, 0.14 mole, Aldrich) was placed in a 250 ml round bottom flask equipped with an overhead stirrer, water condenser, and thermocouple. The acid was heated to 60° C. at which point it was a viscous liquid. To this liquid was added in several two ml portions, $C_3F_7O[CF(CF_3)CF_2O]_nCF(CF_3)CONHC_2H_4OH$, ($M_N$=1220, 50 g, 0.041 mole, n is equal to 3 to 10). This addition was slightly exothermic.

After the addition was completed, the reaction mixture was held at 60° C. for two hours, Isopropyl acetate (35 ml) was added and the resulting solution then stirred with 150 ml of 2% aqueous HCl for four hours. The lower fluorochemical-containing phase was then separated and dissolved in about 300 ml methyl t-butyl ether (MTBE) and the ether solution then washed twice with an equal volume of 2N HCl solution. The MTBE solution was separated, dried over magnesium sulfate, filtered, and the solvents removed by rotary evaporation. The infrared spectrum of the resulting product showed a strong carbonyl stretch at 1709 cm$^{-1}$. Proton and phosphorus-31 NMR analysis showed that the product was about 75% the desired fluorinated phosphate and 25% unreacted starting amide alcohol.

A portion of the fluorinated phosphate product was diluted to 0.25 wt % in HFE-7100 (methyl perfluorobutyl ether) and shaken to obtain a clear solution. Quarter-wafer pieces of aluminum- and chromium-coated silicon wafers (100 mm diameter, obtained from WaferNet, San Jose, Calif.) were cleaned by 5 min. exposure in a home-built UV/ozone chamber, and immediately treated with the above solution. One aluminum piece was immersed in the solution for 1 hour at room temperature, then rinsed for 1 min. in HFE 7100 and allowed to dry in air. One aluminum and one chromium piece were treated by spin coating the solution (500 rpm/5 sec then 2000 rpm/15 sec), then the coated wafer was heated on a vacuum hotplate at 150° C. for 3 min., rinsed in HFE 7100, and allowed to dry in air.

The wafers were subjected to measurement of water and hexadecane contact angles. Measurements were made using as-received reagent-grade hexadecane (Aldrich) and deionized water filtered through a filtration system obtained from Millipore Corporation (Billerica, Mass.), on a video contact angle analyzer available as product number VCA-2500XE from AST Products (Billerica, Mass.). Reported values are the averages of measurements on at least three drops measured on both sides, and are shown in Table 1. Drop volumes were 5 μL for static measurements and 1-3 μL for advancing and receding. For hexadecane, only advancing and receding contact angles are reported because static and advancing values were found to be nearly equal.

TABLE 1

Water and Hexadecane Contact Angles on Metal-Coated Silicon Wafers

| Substrate | Application[a] | Liquid | Contact Angles (°) | | |
|---|---|---|---|---|---|
| | | | Static | Advancing | Receding |
| Aluminum | 1 hr/RT | Water | 120 | 124 | 115 |
| | " | Hexadecane | — | 76 | 64 |
| | SC/H/R | Water | 117 | 126 | 112 |
| | " | Hexadecane | — | 79 | 61 |
| Chromium | SC/H/R | Water | 135 | 143 | 112 |
| | " | Hexadecane | — | 87 | 50 |

[a]1 hr/RT = 1 hr immersion at room temperature; SC/H/R = spin coated, heated at 150° C./3 min, rinsed.

The above data show that the phosphate compound rendered the surfaces of both metals highly hydrophobic and oleophobic.

Example 2

To make the compound of the following formula:

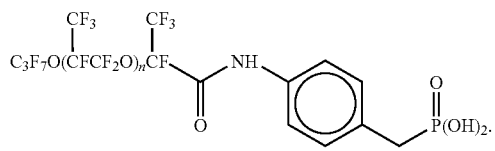

diethyl(4-aminobenzyl)phosphonate (10 g, 0.041 mole, Aldrich), triethylamine (4.15 g, 0.041 mole) and methyl t-butyl ether (100 ml) were combined in a 250 ml round bottom flask equipped with an overhead stirrer and water condenser under nitrogen. To this mixture was added, dropwise over about 1.5 hours, $C_3F_7O[CF(CF_3)CF_2O]_nCF(CF_3)COF$, ($M_W$=1017, 41.8 g, 0.041 mole, prepared by cesium fluoride-initiated oligomerization of hexafluoropropylene oxide in diglyme solvent with distillative removal of low-boiling components, as described in U.S. Pat. No. 3,274,244). Near the end of the addition the solution became nearly homogeneous. After stirring for 16 hours at ambient temperature, the solution was diluted with additional MTBE and washed with about 5% aqueous sodium bicarbonate and then once with 2N HCl. After drying over magnesium sulfate the solvent was removed by rotary evaporation. The amide carbonyl was seen at 1721.5 cm$^{-1}$ in the infrared spectrum of the resulting product.

Without further purification, the phosphonate was dissolved in diethyl ether and bromotrimethylsilane (17.6 g, 0.115 mole, Aldrich) was added all at once. The solution was stirred for 24 hours at ambient temperature and an additional 10 g of the silane added. After several hours, anhydrous methanol was added to decompose the unreacted silane as well as the silyl ester. The solvent was removed from the resulting homogeneous solution and the residue treated two more times with anhydrous methanol in an analogous manner. The final methanol solution after reduction in volume by rotary evaporation was poured into water and the solid phosphonic acid filtered and air-dried. Analysis by proton, phosphorus-31, and carbon-13 NMR confirmed the structure.

Example 3

To make the compound of the following formula

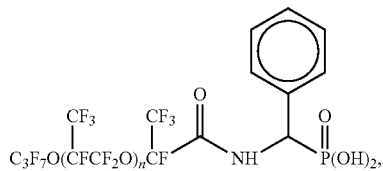

diethyl(α-aminobenzyl)phosphonate hydrochloride (10.5 g, 0.037 mole, Aldrich), triethylamine (7.58 g, 0.075 mole), and MTBE (100 ml) were combined in a 250 ml round bottom flask equipped with a magnetic stirrer and water condenser. $C_3F_7O[CF(CF_3)CF_2O]_nCF(CF_3)COF$, ($M_W$=1017, 35 g, 0.034 mole) was added in one portion and the resulting mixture stirred for 16 hours at ambient temperature. No remaining acid fluoride was observed by infrared analysis at the end of this reaction period. Water was added and the lower fluorochemical-containing phase separated and washed two more times with dilute HCl in order to remove any residual triethylamine salts as well as unreacted phosphonate starting material. The solvent was removed via rotary evaporation and then treated with bromotrimethylsilane (21 g, 0.14 mole). In this case a small amount of diethyl ether was added and the solution refluxed for six hours and then stirred for an additional 18 hours at ambient temperature.

The workup of the composition followed that described above in Example 2. However it was found that this procedure was insufficient to completely hydrolyze the diethyl phosphonate. The partially hydrolyzed mixture (20.2 g) was then treated with an additional 20 g bromotrimethysilane and heated to reflux (about 80° C.) for eighteen hours. The removal of the silyl ester by the addition of several portions of methanol proceeded as described in Example 2 although the final product was not precipitated from water. The infrared spectrum of the product showed a carbonyl peak at 1712 cm$^{-1}$. The structure was confirmed by proton, fluorine-19, and carbon-13 NMR analysis.

Example 4

The materials prepared in Example 3 and in Example 1 were each diluted to 0.1 wt % in HFE 7100 and shaken to obtain clear solutions. The material prepared in Example 2 could not be readily dissolved directly into HFE 7100, so it was first diluted to 5 wt % in isopropyl alcohol and shaken to dissolve the solid. This solution was filtered through a 0.45 μm filter cartridge to remove a small amount of undissolved material. The resulting clear solution (4.97 wt % solids by gravimetry) was diluted (1 g) with 49 g HFE-7100 to prepare a 0.1 wt % solution, which was clear and storage-stable with respect to formation of precipitate for at least several weeks at room temperature.

Three quarter-wafer pieces each of aluminum- and chromium-coated silicon wafers (100 mm diameter, obtained from WaferNet, San Jose, Calif.) were cleaned by 5 min exposure in a home-built UV/ozone chamber, and immediately treated with the above solutions by spin coating. This was done by applying 2 ml coating solution by pipette to the wafer while it was spinning at 2000 rpm. The wafers were then heated on a vacuum hotplate at 150° C. for 3 min., allowed to cool, then rinsed for 1 min in HFE-7100 and allowed to dry in air. Water contact angles were measured using the procedures and apparatus described in Example 1. Results appear in Table 2.

TABLE 2

Water Contact Angles for Coatings on Aluminum and Chromium Substrates

| Compound | Substrate | Static CA (°) | Adv CA (°) | Rec CA (°) |
|---|---|---|---|---|
| Example 2 | Aluminum | 120 | 123 | 114 |
| | Chromium | 133 | 140 | 110 |
| Example 3 | Aluminum | 122 | 125 | 105 |
| | Chromium | 130 | 140 | 113 |
| Example 1 | Aluminum | 122 | 126 | 117 |
| | Chromium | 132 | 139 | 111 |

Example 5

Samples of the materials prepared in Examples 2 and 3 were each diluted to 0.2 wt % in isopropyl alcohol and shaken to obtain clear solutions. Four quarter-wafer pieces of aluminum-coated silicon wafer (100 mm diameter, obtained from WaferNet, San Jose, Calif.) were cleaned by 5 min exposure in a home-built UV/ozone chamber, and immediately treated with the above solutions. Two pieces were treated with each solution, one by 1 hour immersion at room temperature followed by 1 min. rinse in isopropyl alcohol, the other by spin coating (500 rpm/5 sec. then 2000 rpm/15 sec.) followed by heating 3 min. at 150° C. on a vacuum hotplate, then rinsing 1 min. in isopropyl alcohol. The coated wafer pieces were blown dry under nitrogen, then subjected to measurement of water contact angles using the procedures and apparatus described in Example 1. Results appear in Table 3.

TABLE 3

Water Contact Angles on Aluminum-Coated Silicon Wafers

| Compound | Application[a] | Static CA (°) | Adv CA (°) | Rec CA (°) |
|---|---|---|---|---|
| Example 2 | 1 hr/RT | 115 | 124 | 92 |
| | SC/H/R | 111 | 123 | 92 |
| Example 3 | 1 hr/RT | 103 | 112 | 57 |
| | SC/H/R | 99 | 114 | 65 |

[a] 1 hr/RT = 1 hr immersion at room temperature; SC/H/R = spin coat, heat 150° C./3 min, rinse.

Comparison of these data with results from Example 1 shows that coatings with higher contact angles were obtained using HFE 7100 as the solvent.

Although the present invention has been described with reference to specific Figures and embodiments, workers skilled in the art will recognize that changes may be made in form and detail without departing from the spirit and scope of the invention.

We claim:

1. A composition comprising organic solvent and a compound dissolved or dispersed the organic solvent, the compound according to Formula I:

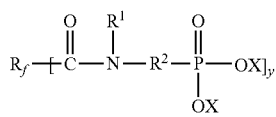

I wherein $R_f$ is a monovalent or divalent perfluoropolyether group;

y is equal to 1 or 2;

each X is independently hydrogen, alkyl, cycloalkyl, alkali metal, ammonium, ammonium substituted with an alkyl or cycloalkyl, or a five to seven membered heterocyclic group having a positively charged nitrogen atom;

$R^1$ is hydrogen or alkyl; and $R^2$ is a divalent group selected from an alkylene, arylene, or combinations thereof optionally containing a divalent group selected from carbonyl, carbonyloxy, carbonylimino, sulfonamido, or combinations thereof, wherein alkylene optionally contains at least one ether group, and wherein $R^2$ is unsubstituted or substituted with an alkyl, aryl, halo, or combinations thereof.

2. The composition of claim 1, wherein $R^2$ comprises a phenylene group bonded to an alkylene group having 1 to 6 carbon atoms.

3. The composition of claim 1, wherein $R^2$ comprises an alkylene group having 1 to 6 carbon atoms, said alkylene group being unsubstituted or substituted with a phenyl group or an alkyl group.

4. The composition of claim 1, wherein $R_f$ is monovalent and selected from $C_3F_7O(CF(CF_3)CF_2O)_nCF(CF_3)$—, $C_3F_7O(CF_2CF_2CF_2O)_nCF_2CF_2$—, or $CF_3O(C_2F_4O)_nCF_2$— where n has an average value of 0 to 50.

5. The composition of claim 1, wherein the compound is of formula

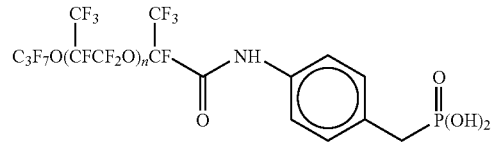

or a salt or ester thereof, wherein n has an average value of 3 to 30.

6. The composition of claim 1, wherein the compound is of formula

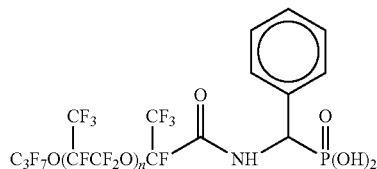

or a salt or ester thereof, wherein n has an average value of 3 to 30.

7. The composition of claim 1, wherein the compound is of formula

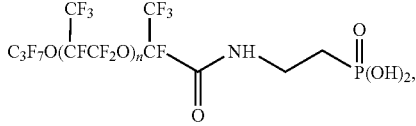

-continued

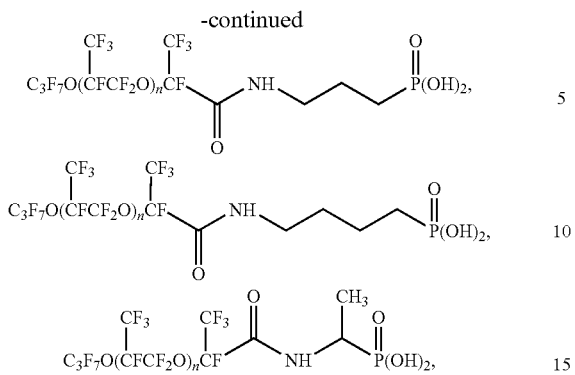

or a salt or ester thereof, wherein n has an average value of 3 to 30.

8. The composition of claim 1, wherein each X is independently hydrogen, alkyl, cycloalkyl, or alkali metal.

9. The composition of claim 1, wherein each X is independently hydrogen, alkyl, or cycloalkyl.

10. A composition comprising a hydrofluoroether and a compound according to Formula I, Formula II, or combinations thereof:

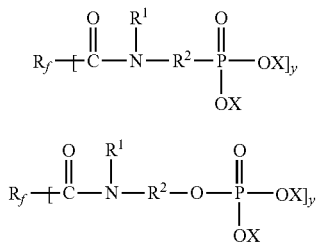

wherein
R$_f$ is a monovalent or divalent perfluoropolyether group;
y is equal to 1 or 2;
each X is independently hydrogen, alkyl, cycloalkyl, alkali metal, ammonium, ammonium substituted with an alkyl or cycloalkyl, or a five to seven membered heterocyclic group having a positively charged nitrogen atom;
R$^1$ is hydrogen or alkyl; and
R$^2$ comprises a divalent group selected from an alkylene, arylene, heteroalkylene, or combinations thereof and an optional divalent group selected from carbonyl, carbonyloxy, carbonylimino, sulfonamido, or combinations thereof, wherein R$^2$ is unsubstituted or substituted with an alkyl, aryl, halo, or combinations thereof;

wherein the hydrofluoroether is represented by formula

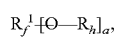

wherein
a is an integer of 1 to 3;
R$_f^1$ is a monovalent, divalent, or trivalent radical of a perfluoroalkane, perfluoroether, or perfluoropolyether; and
R$_h$ is an alkyl or heteroalkyl.

11. The composition of claim 10, wherein the composition includes at least one compound selected from

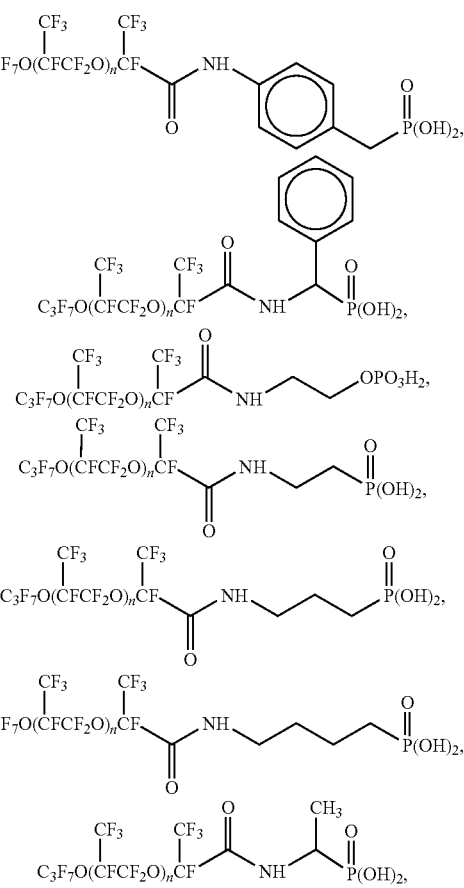

or a salt or ester thereof, wherein n has an average value of 3 to 30.

12. The composition of claim 10, wherein the hydrofluoroether is a methyl perfluorobutyl ether or a ethyl perfluorobutyl ether.

13. A composition comprising a fluorinated silane, and a compound according to Formula I, Formula II, or combinations thereof dissolved or dispersed in an organic solvent:

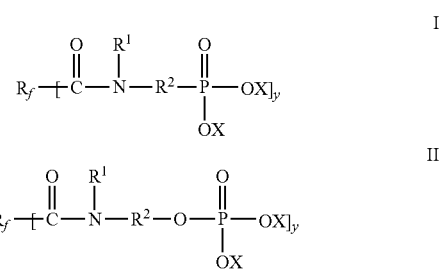

wherein
R$_f$ is a monovalent or divalent perfluoropolyether group;
y is equal to 1 or 2;
each X is independently hydrogen, alkyl, cycloalkyl, alkali metal, ammonium, ammonium substituted with an alkyl or cycloalkyl, or a five to seven membered heterocyclic group having a positively charged nitrogen atom;
R$^1$ is hydrogen or alkyl; and R² comprises a divalent group selected from an alkylene, arylene, or combinations thereof optionally containing a divalent group selected from carbonyl, carbonyloxy, carbonylimino, sulfonamido, or combinations thereof, wherein alkylene optionally contains at least on ether group, and wherein R² is unsubstituted or substituted with an alkyl, aryl, halo, or combinations thereof.

14. The composition of claim 13, wherein the composition comprises at least one compound of formula

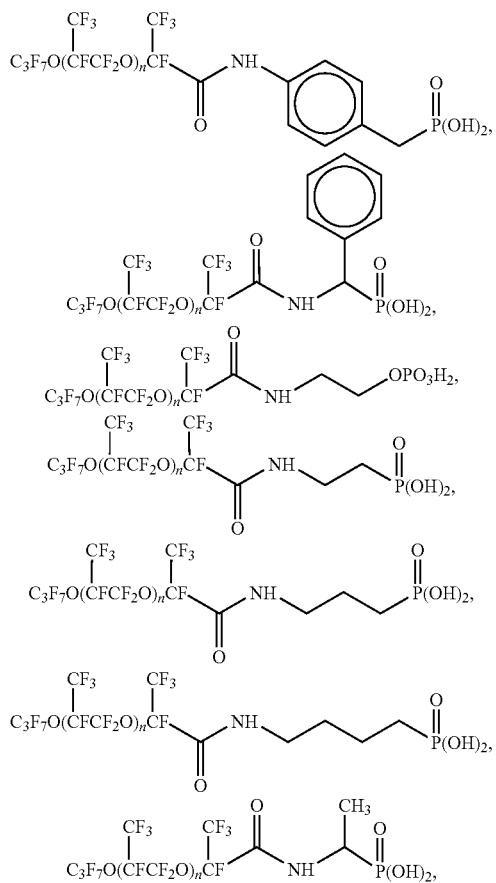

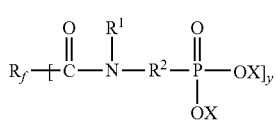

or a salt or ester thereof, wherein n has an average value of 3 to 30.

15. A non-aqueous composition comprising a compound dissolved or dispersed in organic solvent, said compound being of Formula I:

$$R_f \!\!-\!\![C(=O)\!-\!N(R^1)\!-\!R^2\!-\!P(=O)(OX)\!-\!OX]_y$$

wherein
  $R_f$ is a monovalent or divalent perfluoropolyether group;
  y is equal to 1 or 2;
  each X is independently hydrogen, alkyl, alkali metal, ammonium, ammonium substituted with an alkyl or cycloalkyl, or a five to seven membered heterocyclic group having a positively charged nitrogen atom;
  $R^1$ is hydrogen or alkyl; and R² is a divalent group selected from an alkylene, arylene, or combinations thereof optionally containing a divalent group selected from carbonyl, carbonyloxy, carbonylimino, sulfonamido, or combinations thereof, wherein alkylene optionally contains at least one ether group, and wherein R² unsubstituted or substituted with an alkyl, aryl, halo, or combinations thereof.

16. The non-aqueous composition of claim 15, wherein the compound is of formula

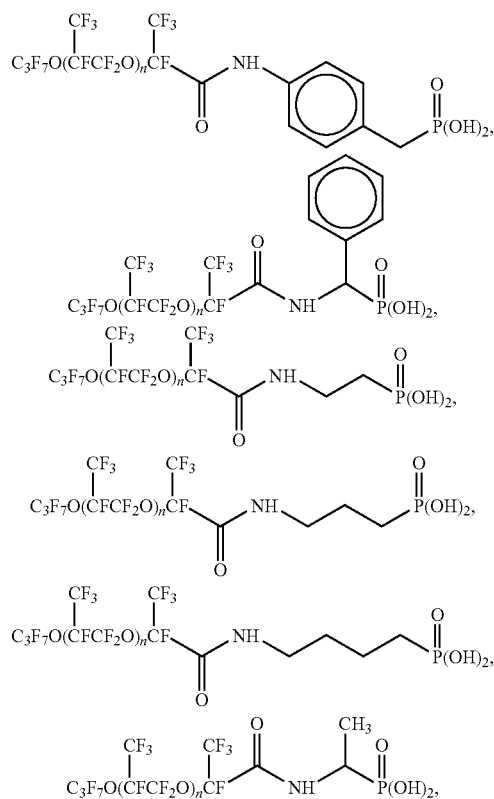

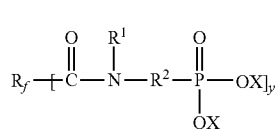

or a salt or ester thereof, wherein n has an average value of 3 to 30.

17. A method of reducing contaminant adhesion to a substrate, said method comprising applying a coating composition to a surface of the substrate, said coating composition comprising organic solvent and a compound dissolved or dispersed in the organic solvent, the compound according to Formula I, Formula II, or combinations thereof:

$$R_f\!\!-\!\![C(=O)\!-\!N(R^1)\!-\!R^2\!-\!P(=O)(OX)\!-\!OX]_y \quad \text{I}$$

$$R_f\!\!-\!\![C(=O)\!-\!N(R^1)\!-\!R^2\!-\!O\!-\!P(=O)(OX)\!-\!OX]_y \quad \text{II}$$

wherein
  $R_f$ is a monovalent or divalent perfluoropolyether group;
  y is equal to 1 or 2;

each X is independently hydrogen, alkyl, alkali metal, ammonium, ammonium substituted with an alkyl or cycloalkyl, or a five to seven membered heterocyclic group having a positively charged nitrogen atom;

$R^1$ is hydrogen or alkyl; and $R^2$ comprises a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof.

18. The method of claim 17, wherein the coating composition includes at least one compound of formula

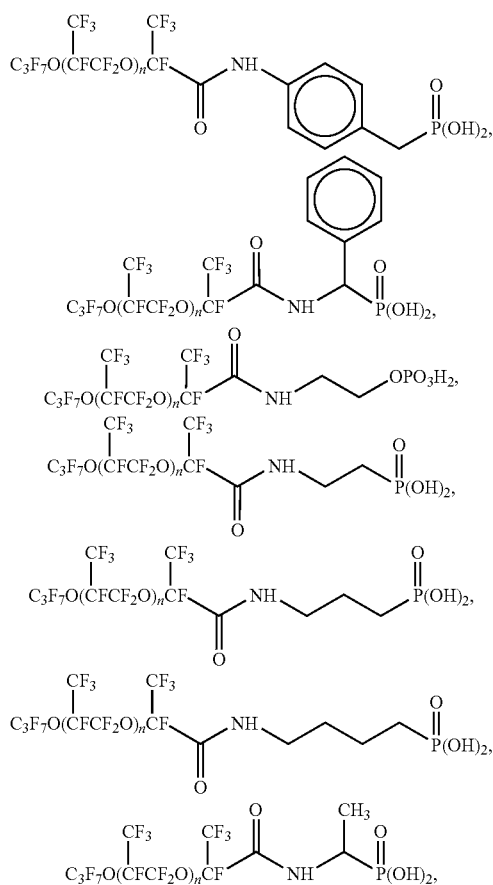

or a salt or ester thereof, wherein n has an average value of 3 to 30.

19. A method of making an article, said method comprising applying a coating composition to a surface of the article, said coating composition comprising organic solvent and a dissolved or dispersed in the organic solvent, the compound according to Formula I:

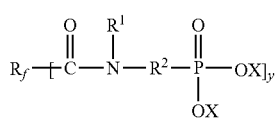

wherein $R_f$ is a monovalent or divalent perfluoropolyether group;

y is equal to 1 or 2;

each X is independently hydrogen, alkyl, alkali metal, ammonium, ammonium substituted with an alkyl or cycloalkyl, or a five to seven membered heterocyclic group having a positively charged nitrogen atom;

$R^1$ is hydrogen or alkyl; and $R^2$ comprises a divalent group selected from an alkylene, arylene, heteroalkylene, or combinations thereof and an optional divalent group selected from carbonyl, carbonyloxy, carbonylimino, sulfonamido, or combinations thereof, wherein $R^2$ is unsubstituted or substituted with an alkyl, aryl, halo, or combinations thereof.

20. The method of claim 19, wherein the coating composition includes at least one compound of formula

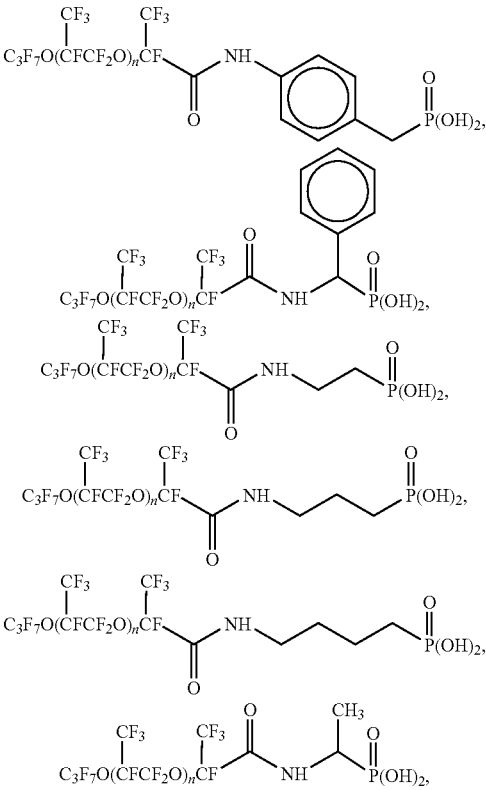

or a salt or ester thereof, wherein n has an average value of 3 to 30.

21. A method of making an article, said method comprising applying a coating composition to a surface of the substrate, said coating composition comprising a first component and a second component dissolved or dispersed in organic solvent:

a) the first component selected from a hydrofluoroether, fluorinated silane, or combinations thereof: and b) the second component selected from a compound according to Formula I, Formula II, or a combination of compounds according to Formulas I and II:

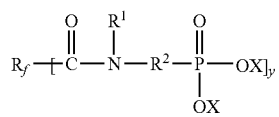

-continued

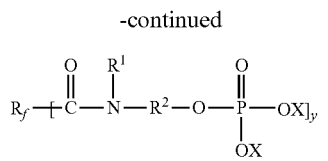
II wherein
R$_f$ is a monovalent or divalent perfluoropolyether group;
y is equal to 1 or 2;
each X is independently hydrogen, alkyl, alkali metal, ammonium, ammonium substituted with an alkyl or cycloalkyl, or a five to seven membered heterocyclic group having a positively charged nitrogen atom;
R$^1$ is hydrogen or alkyl; and
R$^2$ is a divalent group selected from an alkylene, arylene, or combinations thereof optionally containing a divalent group selected from carbonyl, carbonyloxy, carbonylimino, sulfonamido, or combinations thereof, wherein alkylene optionally contains at least one ether group, and wherein R$^2$ is unsubstituted or substituted with an alkyl, aryl, halo, or combinations thereof;
wherein the hydrofluoroether is represented by formula

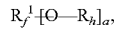

wherein
a is an integer of 1 to 3;
R$_f^1$ is a monovalent, divalent, or trivalent radical of a perfluoroalkane, perfluoroether, or perfluoropolyether; and
R$_h$ is an alkyl or heteroalkyl.

22. The method of claim 21, wherein the coating composition includes at least one compound of formula

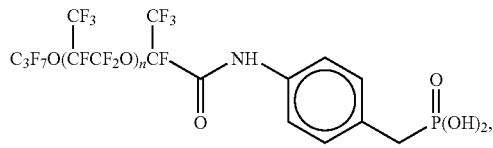

-continued

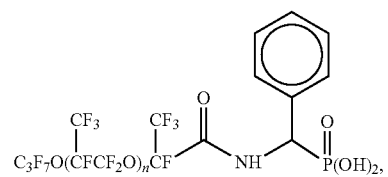

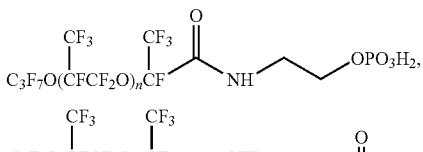

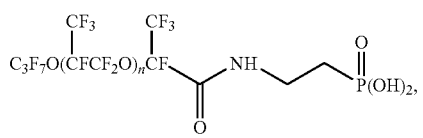

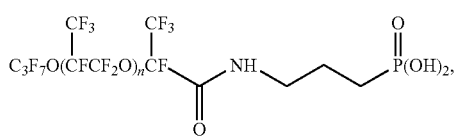

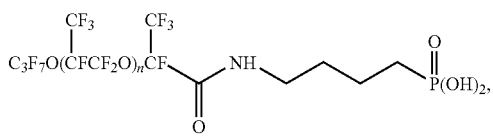

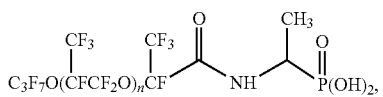

or a salt or ester thereof, wherein n has an average value of 3 to 30.

23. The method of claim 21, wherein the coating composition reduces contaminant adhesion to the surface.

* * * * *